United States Patent
McCarthy et al.

(10) Patent No.: US 9,597,124 B2
(45) Date of Patent: Mar. 21, 2017

(54) SPINAL CORRECTION SYSTEM AND METHOD

(71) Applicant: Warsaw Orthopedic, Inc., Warsaw, IN (US)

(72) Inventors: Richard E McCarthy, Little Rock, AR (US); Brian A. Butler, Atoka, TN (US); Joshua W. Simpson, Collierville, TN (US); Gary S. Lindemann, Collierville, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 211 days.

(21) Appl. No.: 14/151,049

(22) Filed: Jan. 9, 2014

(65) Prior Publication Data
US 2015/0190174 A1    Jul. 9, 2015

(51) Int. Cl.
*A61B 17/88* (2006.01)
*A61B 17/70* (2006.01)

(52) U.S. Cl.
CPC .................. *A61B 17/707* (2013.01)

(58) Field of Classification Search
CPC ............ A61B 17/7032; A61B 17/7001; A61B 17/705; A61B 17/7035; A61B 17/7008
USPC .................................................. 606/250–279
See application file for complete search history.

(56) References Cited

U.S. PATENT DOCUMENTS

| | | | | |
|---|---|---|---|---|
| 5,507,745 A | * | 4/1996 | Logroscino | A61B 17/7055 606/261 |
| 5,989,251 A | * | 11/1999 | Nichols | A61B 17/7049 606/246 |
| 7,338,490 B2 | * | 3/2008 | Ogilvie | A61B 17/7053 606/276 |
| 7,485,133 B2 | * | 2/2009 | Cannon | A61B 17/7056 606/246 |
| 7,993,371 B2 | * | 8/2011 | Farris | A61B 17/7007 606/246 |
| 2007/0276384 A1 | * | 11/2007 | Spratt | A61B 17/7056 606/276 |
| 2009/0287253 A1 | * | 11/2009 | Felix | A61B 17/7058 606/278 |
| 2012/0158065 A1 | * | 6/2012 | Jouve | A61B 17/7001 606/276 |

* cited by examiner

*Primary Examiner* — Mary Hoffman
*Assistant Examiner* — Tara R Carter

(57) ABSTRACT

A spinal construct comprises at least one spinal implant connected with vertebrae and a member extending between a first end including, at least one part configured for connection to tissue of a rib cage and a second end configured for connection with the at least one spinal implant. Systems and methods are disclosed.

17 Claims, 6 Drawing Sheets

SPINAL CORRECTION SYSTEM AND METHOD

TECHNICAL FIELD

The present disclosure generally relates to medical devices for the treatment of musculoskeletal disorders, and more particularly to a surgical system for correction of a spine disorder.

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, discectomy, laminectomy, fusion, fixation and implantable prosthetics. Correction treatments used for positioning and alignment of vertebrae may employ implants, such as, for example, spinal constructs. The spinal constructs, which may include rods and bone screws, are manipulated with surgical instruments for engagement with vertebrae to position and align one or more vertebrae. This disclosure describes improvements over these prior art technologies.

SUMMARY

In one embodiment, a spinal construct is provided. The spinal construct comprises at least one spinal implant connected with vertebrae and a member extending between a first end including at least one part configured for connection to tissue of a rib cage and a second end configured for connection with the at least one spinal implant. In some embodiments, systems and methods are provided.

BRIEF DESCRIPTION OF THE DRAWINGS

The present disclosure will become more readily apparent from the specific description accompanied by the following drawings, in which.

DETAILED DESCRIPTION

Figure 1:
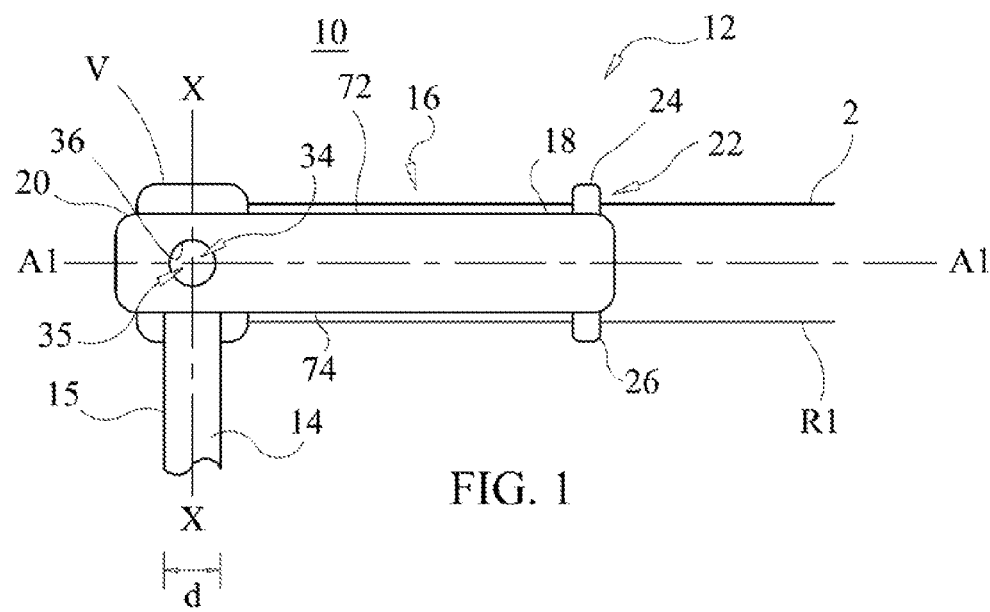
FIG. 1 is a plan view of components of one embodiment of a system in accordance with the principles of the present disclosure.

The exemplary embodiments of the system and related methods of use disclosed are discussed in terms of medical devices for the treatment of musculoskeletal disorders and more particularly, in terms of a surgical system and method for correction of a spine disorder.

In one embodiment, the surgical system includes an outrigger construct attached to tissue of a rib cage and a main construct, such as, for example, bone fasteners and/or spinal rods fixed with vertebrae. In one embodiment, the outrigger construct is placed under a scapula of a patient and muscle mass to prevent the outrigger construct from protruding through skin of the patient. In one embodiment, the surgical system is placed unilaterally. In one embodiment, the surgical system is placed bilaterally. In one embodiment, the surgical system includes a plate that is attached to screws and to the ribs to provide additional support to prevent pullout. In one embodiment, the plate is disposed below the screw, or on a ledge of the screw to prevent back out. In one embodiment, a cap, made of a biocompatible material, is disposed with the screw to fix the rod and the plate in place. In one embodiment, a rod, made of a biocompatible material, can be built into the plate/screw construct that would, constrain the rod but still allow for longitudinal growth of the patient.

In one embodiment, the surgical system includes a hook claw configured for attachment with the lamina and includes a receiving member for the rod. In one embodiment, the plate and hook claw configuration prevents screw back out.

In one embodiment, the surgical system includes a hook claw configured for axial translation and attachable to the outrigger construct.

In some embodiments, one or all of the components of the surgical system may be disposable, peel-pack, pre-packed sterile devices. One or all of the components of the system may be reusable. The system may be configured as a kit with multiple sized and configured components.

In some embodiments, the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the present disclosure may be employed with other osteal and bone related applications, including those associated with diagnostics and therapeutics. In some embodiments, the disclosed system may be alternatively employed in a surgical treatment with a patient in a prone or supine position, and/or employ various surgical approaches to the spine, including anterior, posterior, posterior mid-line, direct lateral, postero-lateral, and/or antero lateral approaches, and in other body regions. The present disclosure may also be alternatively employed with procedures for treating the lumbar, cervical, thoracic and pelvic regions of a spinal column. The system and methods of the present disclosure may also be used on animals, bone models and other non-living substrates, such as, for example, in training, testing and demonstration.

The present disclosure may be understood more readily by reference to the following detailed description of the disclosure taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure. Also, in some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, muscle, vessels, ligaments, tendons, cartilage and/or bone unless specifically referred to otherwise.

Figure 2:
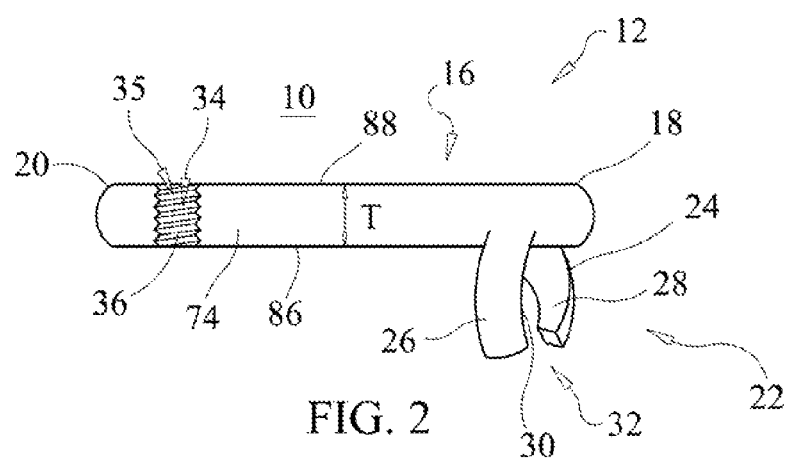
FIG. 2 is a perspective view in part cross-section of components of the system shown in FIG. 1.
Figure 3:
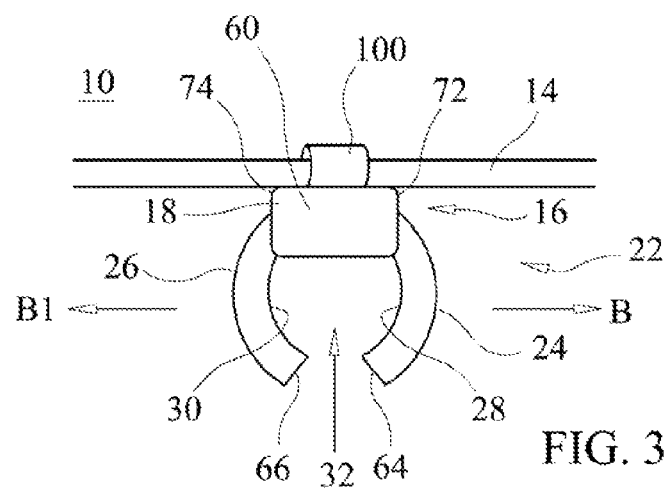
FIG. 3 is a side view of components of the system shown in FIG. 1.

The following discussion includes a description of a system in accordance with the principles of the present disclosure. Alternate embodiments are also disclosed. Reference is made in detail to the exemplary embodiments of the present disclosure, which are illustrated in the accompanying figures. Turning to FIGS. 1-3, there are illustrated components of a system, such as, for example, a spinal correction system 10.

The components of system 10 can be fabricated from biologically acceptable materials suitable for medical applications, including metals, synthetic polymers, ceramics, bone material, tissue and/or their composites, depending on the particular application and/or preference of a medical practitioner. For example, the components of system 10, individually or collectively, can be fabricated from materials such as stainless steel alloys, aluminum, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$^4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of system 10 may have material composites, including the above materials, to achieve various desired characteristics such as strength, rigidity, elasticity, compliance, biomechanical performance, durability and radiolucency or imaging preference. The components of system 10, individually or collectively, may also be fabricated from a heterogeneous material such as a combination of two or more of the above-described materials. The components of system 10 may be monolithically formed, integrally connected or include fastening elements and/or instruments, as described herein.

System 10 includes a spinal construct 12 that is configured for connecting to tissue, such as, for example, tissue of a rib cage R1 and a spinal implant, such as, for example, a spinal rod 14 configured to correct a spinal deformity. Spinal construct 12 is configured to be placed under a scapula of a patient and muscle mass to prevent spinal construct 12 from protruding through skin of the patient. In some embodiments, spinal construct 12 is configured to be employed to treat an undesired curvature of a spine, such as scoliosis, while allowing for growth of the spinal column.

In some embodiments, spinal rod 14 is substantially cylindrical. In some embodiments, spinal rod 14 may have various cross section configurations, such as, for example, oval, oblong, triangular, rectangular, square, polygonal, irregular, uniform, non-uniform, variable and/or tapered. In some embodiments, spinal rod 14 defines an axis X along its length. In one embodiment, spinal rod 14 extends along an axial plane, such as for example, a sagittal plane of a body of a patient. In some embodiments, spinal construct 12 may include one or a plurality of spinal rods 14. In some embodiments, one or all of a plurality of spinal rods 14 may be disposed in various relative orientations, such as, for example, side-by-side, parallel, transverse, perpendicular or angular and/or be disposed to extend along substantially coronal, sagittal and transverse planes of a body.

Spinal rod 14 includes an outer surface 15 defining a uniform thickness/diameter d. In some embodiments, spinal rod 14 may have various surface configurations, such as, for example, rough, threaded for connection with surgical instruments, arcuate, undulating, porous, semi-porous, dimpled, polished and/or textured. In some embodiments, diameter d defined by spinal rod 14 may be uniformly increasing or decreasing, or have alternate diameter d dimensions along its length.

In some embodiments, spinal rod 14 may have various lengths. In some embodiments, spinal rod 14 may be made from autograft and/or allograft and be configured for resorbable or degradable applications. In one embodiment, spinal rod 14 is a cadaver tendon. In one embodiment spinal rod 14 is a tendon that may be harvested, for example, from a patient or donor. In some embodiments, all or only a portion of spinal rod 14 may have a semi-rigid, flexible or elastic configuration and/or have elastic and/or flexible properties similar to the properties from materials, such as, for example, fabric, silicone, polyurethane, silicone-polyurethane, copolymers, rubbers, polyolefin rubber, elastomers, thermoplastic elastomers, thermoset elastomers and elastomeric composites. In one embodiment, spinal rod 14 provides a selective amount of expansion and/or extension in an axial direction. In some embodiments, spinal rod 14 may have a flexible configuration, which includes movement in a lateral or side to side direction. In some embodiments, spinal rod 14 may be compressible in an axial direction. Spinal rod 14 can include a plurality of separately attachable or connectable portions or sections, such as bands or loops, or may be monolithically formed as a single continuous element.

Spinal construct 12 includes a member, such as, for example, a plate 16. In some embodiments, plate 16 is configured to resist and/or prevent pullout of bone fasteners, as described herein, while constraining spinal rod 14 and allowing for longitudinal growth of the patient. Plate 16 extends between an end 18 and an end 20, and defines a longitudinal axis A1. In some embodiments, spinal construct 12 can include one or a plurality of plates 16. Plate 16 has a surface 88 and an opposite surface 86.

In some embodiments, plate 16 has a rectangular configuration and a thickness T defined by a side wall 72 and a side wall 74. In some embodiments, plate 16 has alternate configurations, such as, for example, oval, oblong, triangular, rectangular, square, polygonal, irregular, uniform, non-uniform, variable and/or tapered. In some embodiments, plate 16 may be disposed at alternate orientations, relative to axis X, such as, for example, transverse, and/or other angular orientations such as acute or obtuse, co-axial and/or may be offset or staggered.

Figure 5:
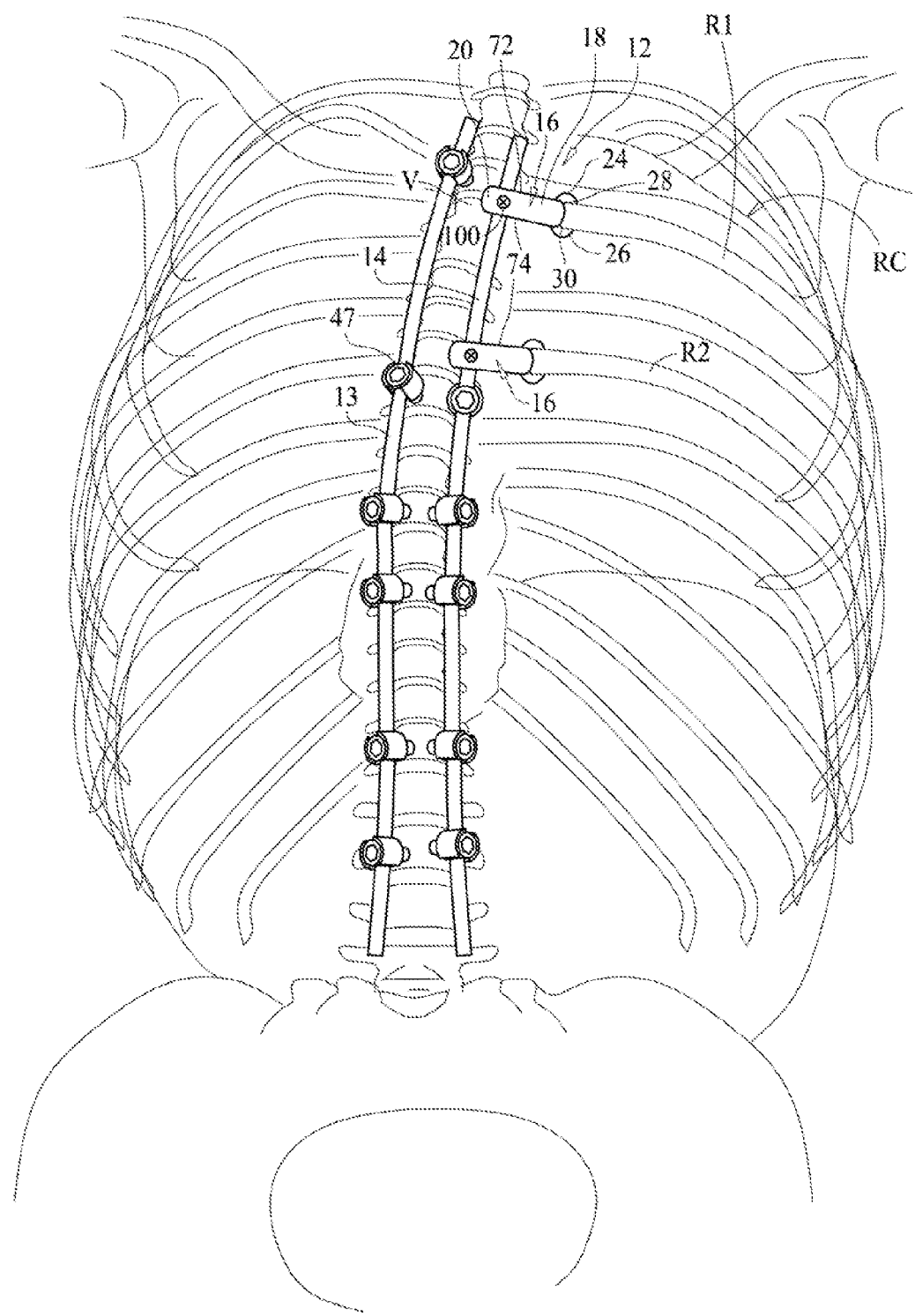
FIG. 5 is a plan view of components of one embodiment of a system in accordance with the principles of the present disclosure disposed with vertebrae.

Plate 6 includes a part, such as, for example, a clip 22 configured for connecting to tissue, such as, for example, a rib R1 of a rib cage (FIG. 5). In some embodiments, components of spinal construct 12 including plate 16 can comprise one or a plurality of clips 22, with each clip 22 being connected with the same or alternate portions of the tissue of a patient. In some embodiments, engagement of clip 22 with tissue includes capture, snap-fit, friction fit, pressure fit, mechanical connection and/or adhesive. Clip 22 extends laterally from end 18 of walls 72, 74. In some embodiments, clip 22 extends laterally from end 20 such as walls 72, 74. In some embodiments, clip 22 extends laterally from both ends 18, 20 of side wall 72, 74. In some embodiments, the part can include a tie-down configuration such that plate 16 is connected to tissue and fastened therewith via a wire and/or synthetic tether.

Clip 22 has a claw configuration including a pair of resilient, inwardly biased arms, such as, for example, a hook 24 and a hook 26. Hooks 24, 26 extend from end 18. In some embodiments, components of spinal construct 12 including plate 16 can include one or a plurality of hooks 22 being connected with the same or alternate portions of the tissue of a patient. In some embodiments, hooks 24, 26 are configured for direct connection to plate 16 and pivotally movable therefrom.

Hooks 24, 26 are configured to connect to a pivot point 60 adjacent a tissue cavity 32. In some embodiments, the material of clip 22 adjacent pivot point 60 includes an elastic and/or resilient configuration so that hooks 24, 26 are engageable for disposal and biased to selected configurations, as described herein. Hook 24 includes a beveled surface 64 and hook 26 includes a bevel surface 66 opposite pivot point 60 to facilitate insertion of tissue into tissue cavity 32, as will be discussed. In some embodiments, all or only a portion of bevels 64, 66 may have various surface configurations, such as, for example, rough, arcuate, undulating, porous, semi-porous, dimpled, polished and/or textured, to enhance engagement of tissue. In some embodiments, bevels 64, 66 may be variously configured and dimensioned, such as, for example, planar, concave, convex, polygonal, irregular, uniform, non-uniform, staggered, tapered, consistent or variable. In some embodiments, clip 22 may be disposed at alternate orientations relative to axis A1, such as, for example, transverse and/or other angular orientations, such as, acute or obtuse, according to the requirements of a particular application.

Hook 24 includes a surface 28. Hook 26 includes a surface 30. In some embodiments, all or only a portion of surfaces 28, 30 may have alternate surface configurations, such as, for example, planar, rough, undulating, porous, semi-porous, dimpled, polished and/or textured. Surfaces 28, 30 each have an arcuate configuration defining tissue cavity 32 configured to capture tissue of the rib cage therebetween. Tissue cavity 32 is movable between an expandable orientation to receive tissue, such as, for example, rib R1 such that surfaces 28, 30 space apart to receive tissue and biased to a contracted orientation such that surfaces 28, 30 engage tissue for capture of tissue with hooks 24, 26, as described herein. In some embodiments, surfaces 28, 30 are configured to facilitate the relative movement of hooks 24, 26 and expansion of tissue cavity 32 such that surfaces 28, 30 are movable to dispose tissue with hooks 24, 26. In some embodiments, hooks 24, 26 are variously configured, such as, for example, round, oval, oblong, irregular, uniform, non-uniform, consistent, variable, horseshoe shape, U-shape or kidney bean shape.

In some embodiments, surface 28 is oriented in a first direction and surface 30 is oriented in a second, opposite direction such that surfaces 28, 30 face each other and are configured to engage opposite sides of an outer surface of a rib R1 of a rib cage RC. In some embodiments, surfaces 28, 30 define an adjustable tissue cavity 32 configured for selective capture of tissue about rib R1. In some embodiments, tissue cavity 32 is configured to have a cross sectional area selectively adjustable to be substantially equal to a cross sectional area of a rib R1 In some embodiments, tissue cavity 32 is variously configured, such as, for example, oval, oblong, triangular, rectangular, square, polygonal, irregular, uniform, non-uniform, horseshoe shape, U-shape, kidney bean shape, variable and/or tapered.

In some embodiments, the material of clip 22 adjacent pivot point 60 and/or hooks 24, 26 are, for example, a pliable, flexible, spring-like material and/or a material configured to retain its configuration, such as, for example, Nitinol, relative to plate 16. In some embodiments, surfaces 28, 30 can be roughened or textured to facilitate engagement with tissue. In some embodiments, surfaces 28, 30 can include a layer of adherent material, such as, for example, rubber, to facilitate engagement with tissue.

In some embodiments, hook 24 is configured to be movable relative to hook 26 such that clip 22 is expandable from a first, non-expanded, collapsed or contracted configuration, as shown in FIGS. 2-3, to a second, expanded or spaced apart configuration, as shown in FIG. 1 to engage tissue for disposal of rib R1 with hooks 24, 26. In some embodiments, initially, clip 22 is disposed in a non-expanded configuration due to the resilient spring bias of hooks 24, 26 to a contracted orientation, described herein. In some embodiments, the cross sectional area of tissue cavity 32 in a non-expanded configuration is less than the cross sectional area of rib R1 such that rib R1 is releasably retained with clip 22.

In some embodiments, rib R1 engages surfaces 28, 30 adjacent tissue cavity 32 to overcome the spring bias of hooks 24, 26. As rib R1 is translated into tissue cavity 32 and engages surfaces 28, 30, hooks 24, 26 pivot about pivot point 60 of clip 22 and rotate relative to plate 16, as shown in FIG. 1, and hooks 24, 26 expand, in the direction shown by arrows B, B1. In the expanded configuration, hooks 24, 26 expand such that rib R1 is disposed within expanded tissue cavity 32. The spring bias of hooks 24, 26 cause surfaces 28, 30 to engage an outer surface 2 of rib R1 in a pressure or friction fit such that clip 22 captures rib R1 in a releasable engagement.

In some embodiments, to release rib R1 from clip 22, hooks 24, 26 are manipulated to disengage clip 22 from rib R1. Surfaces 28, 30 disengage from outer surface 2 of rib R1 and rib R1 exits tissue cavity 32. The spring bias of hooks 24, 26 cause hooks 24, 26 to contract such that hook 24 rotates toward hook 26 and clip 22 is disposed in the non-expanded configuration, as described herein.

Figure 4:
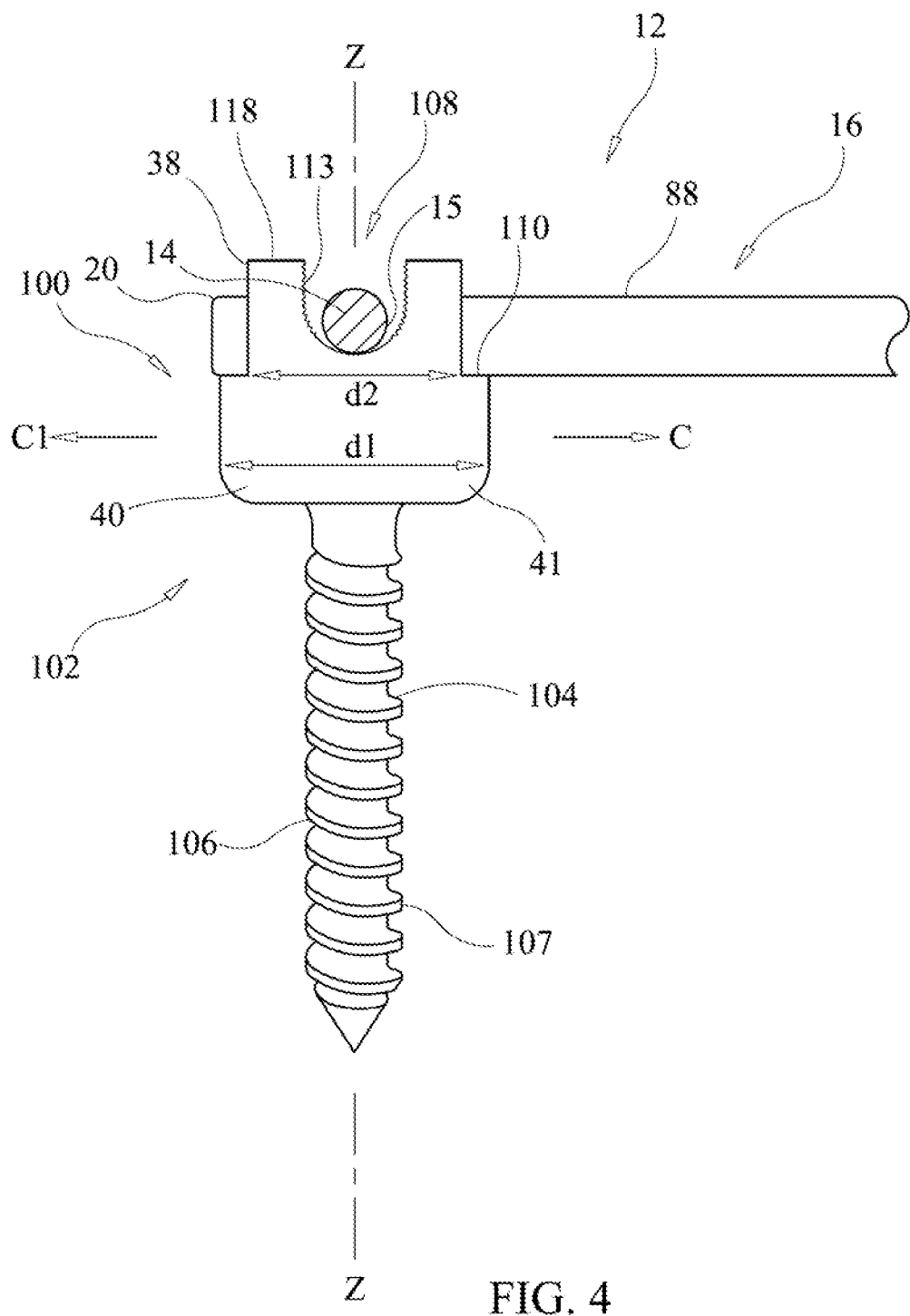
FIG. 4 is a perspective view in part cross-section of components of one embodiment of a system in accordance with the principles of the present disclosure.

End 20 is configured for connection with spinal rod 14, fixed with vertebrae V and to couple plate 16 with spinal rod 14. Spinal rod 14 is coupled with plate 16 and fixed with vertebrae with bone fastener 100, as shown in FIG. 4. End 20 includes a cavity 35 having a threaded inner surface 36 defining a passageway 34. Cavity 35 extends transverse to axis A1. Passageway 34 extends through a surface 88 and an opposite surface 86, as shown in FIG. 2. In some embodiments, passageway 34 is configured for disposal of a fastener, such as, for example, a bone fastener 100, as shown in FIG. 4. Bone fastener 100 is engageable with surface 36 and surface 15 of spinal rod 14 such that plate 16 is detachably locked with spinal rod 14 in a selected position along spinal rod 14.

In some embodiments, system 10 includes a plurality of bone fasteners 100 configured for disposal with tissue, such as, for example, vertebrae V, and engageable with spinal rod 14. In one embodiment, as shown in FIG. 4, bone fastener 100 includes a head 102 configured for attachment with spinal rod 14, and a shaft 104 configured for penetrating tissue. Head 102 includes a base 41 defined by an outer surface 40. Head 102 includes a pair of spaced apart arms 118 defined by an outer surface 38 and an inner surface 113.

Inner surface 113 defines an implant cavity 108. Implant cavity 108 extends through head 102 and is configured for sliding disposal of spinal rod 14. In some embodiments, implant cavity 108 has a cross sectional configuration corresponding to the cross sectional configuration of spinal rod 14 to resist and/or prevent rotation of spinal rod 14 therein. In some embodiments, implant cavity 108 has a cross sectional area substantially equal to a cross sectional area of spinal rod 14 such that spinal rod 14 is axially translatable through implant cavity 108 relative to plate 16.

In some embodiments, inner surface 113 includes a layer of friction-reducing material (not shown). In some embodiments, the layer may include an insert and/or coating comprising silicone, poly(tetrafluororthene), lubricants and/or material examples as described herein. In some embodiments, the layer of friction-reducing material provides an even interface between inner surface 113 and outer surface 15. In some embodiments, all or only a portion of inner surface 113 may have alternate surface configurations, such as, for example, planar, rough, undulating, porous, semi-porous, dimpled, polished and/or textured.

Head 102 includes a shoulder 110, extending from base 41 configured for disposal of plate 16, as shown in FIG. 4. Shoulder 110 extends radially, in the direction shown by arrows C, C1, such that shoulder 110 extends circumferentially around arms 118. In some embodiments, head 102 has an outer diameter d1 defined by base 41 and an outer diameter d2 defined by arms 118. In some embodiments, shoulder 110 extends radially, in the direction shown by arrows C, C1 such that diameter d1 is greater than diameter d. In some embodiments, shoulder 110 is planar. In some embodiments, all or only a portion of shoulder 110 may have various surface configurations, such as, for example, rough, arcuate, undulating, porous, semi-porous, adhesive, dimpled, polished and/or textured, to enhance engagement with a member, such as, for example, plate 16. In some embodiments, shoulder 110 may be variously configured and dimensioned, such as, for example, planar, concave, convex, polygonal, irregular, uniform, non-uniform, staggered, tapered, consistent or variable. In some embodiments, plate 16 can be alternatively positioned to sit below a bone fastener.

In some embodiments, shaft 104 is configured with a cylindrical cross section and includes an outer surface 106 having an external thread form 107. In some embodiments, external thread form 107 may include a single thread turn or a plurality of discrete threads. In some embodiments, other engaging structures may be disposed on shaft 104, such as, for example, a nail configuration, barbs, expanding elements, raised elements and/or spikes to facilitate engagement of shaft 104 with tissue, such as, for example, vertebrae V.

In some embodiments, all or only a portion of shaft 104 may have alternate cross section configurations, such as, for example, oval, oblong, triangular, square, polygonal, irregular, uniform, non-uniform, offset, staggered, undulating, arcuate, variable and/or tapered. In some embodiments, outer surface 106 may include one or a plurality of openings. In some embodiments, all or only a portion of the outer surface 106 may have alternate surface configurations to enhance fixation with tissue such as, for example, rough, arcuate, undulating, mesh, porous, semi-porous, dimpled and/or textured. In some embodiments, all or only a portion of shaft 104 may be disposed at alternate orientations, relative to a longitudinal axis Z of bone fastener 100, such as, for example, transverse, perpendicular and/or other angular orientations such as acute or obtuse, co-axial and/or may be offset or staggered. In some embodiments, all or only a portion of shaft 104 may be cannulated.

In some embodiments, shaft 104 may be configured for attachment to bone, such as cervical, thoracic, lumbar and or sacral vertebral bone structures, or other tissues. In one embodiment, shaft 104 may be a screw, or could also be alternatively configured, for example, as a vertebral hook or clamp. In some embodiments, the threads may be selftapping or intermittent, or may have more than one crest winding about shaft 104. In one embodiment, outer surface 106 may include an opening for accommodating a tool (not shown) for gripping or turning the bone fastener 100.

In some embodiments, system 10 can include one or more of fasteners 100 engaged with tissue in various orientations, such as, for example, series, parallel, offset, staggered and/or alternate vertebral levels. In some embodiments, one or more of fasteners 100 may comprise multi-axial screws, sagittal angulation screws, pedicle screws, mono-axial screws, uni-planar screws, facet screws, fixed screws, tissue penetrating screws, conventional screws, expanding screws, wedges, anchors, buttons, clips, snaps, friction fittings, compressive fittings, expanding rivets, staples, nails, adhesives, posts, fixation plates and/or posts.

In some embodiments, in operation, spinal construct 12 is positioned under a scapula of a patient and muscle mass to prevent spinal construct 12 from protruding through skin of the patient. A practitioner manipulates spinal construct 12, such as, for example, spinal rod 14 and plate 16 to fix and/or attach spinal construct 12 with tissue, such as, for example, rib R1 of a rib cage RC, as shown in FIG. 5. Bone fastener 100 is engageable with threaded inner surface 36 of plate 16 and spinal rod 14 such that plate 16 is detachably locked with spinal rod 14 in a selected position along spinal rod 14. Bone fastener 100 is fixed to vertebrae V and plate 16 and spinal rod 14 are disposed with bone fastener 100 therein. Outer surface 15 of spinal rod 14 engages inner surface 113 of head 102 such that plate 16 can be translated along spinal rod 14 to a desired position.

Plate 16 is translated along a coronal plane of the body to engage surfaces 28, 30 of hooks 24, 26 with tissue, such as, for example, rib R1 of rib cage RC. In one embodiment, plate 16 is rotatable relative to spinal rod 14 in a coronal plane of vertebrae V. Hooks 24, 26 are manipulated such that rib R1 is disposed in tissue cavity 32 and clip 22 is connected with rib R1 such that rib R1 is captured between hooks 24, 26. Clip 22 is positioned such that hooks 24, 26 are disposed in contact with rib R1. A force is applied to clip 22, in a direction transverse to longitudinal axis A1 as shown in FIG. 1, such that hooks 24, 26 space apart to translate over rib R1 and fit around rib R1 such that rib R1 is disposed and provisionally locked within tissue cavity 32. An outer surface 2 of rib R1 engages surfaces 28, 30 of clip 22 such that rib R1 is disposed in tissue cavity 32 of clip 22.

In assembly, operation and use, a spinal correction system 10, similar to the systems and methods described herein, is employed with a surgical correction procedure. For example, spinal correction system 10 may be employed in surgical procedures for treating disorders of the spine, such as, for example, undesirable curvatures of a spine of a child or adolescent requiring, as shown in some embodiments of the present disclosure, a dynamic spinal stabilization system to accommodate a growing spinal column.

In some embodiments, one or all of the components of spinal correction system 10 can be delivered or implanted as a pre-assembled device or can be assembled in situ. The components of spinal correction system 10 may be completely or partially revised, removed or replaced. For example, spinal correction system 10 can be employed with a surgical correction treatment of an applicable condition or injury of an affected section of a spinal column and adjacent areas within a body, such as, for example, vertebrae V, as shown in FIG. 5.

In use, to treat a selected section of vertebrae V, a medical practitioner obtains access to a surgical site including vertebrae V in any appropriate manner, such as through incision and retraction of tissues. In some embodiments, spinal correction system 10 can be used in any existing surgical method or technique inducting open surgery, mini-open surgery, minimally invasive surgery and percutaneous surgical implantation, whereby vertebrae V is accessed through a mini-incision, or sleeve that provides a protected passageway to the area. Once access to the surgical site is obtained, the particular surgical procedure can be performed for treating the spine disorder.

An incision is made in the body of a patient and a cutting instrument (not shown) creates a surgical pathway for implantation of components of spinal correction system 10. A preparation instrument (not shown) can be employed to prepare tissue surfaces of vertebrae V, as well as for aspiration and irrigation of a surgical region.

Bone fasteners 100 are delivered along the surgical pathway to a surgical site that includes vertebrae V. Bone fasteners 100 are delivered adjacent vertebrae V. Shafts 104 of bone fasteners 100 are oriented with the bony anatomy of vertebrae V and a driver (not shown) is manipulable to drive, torque, insert or otherwise fasten bone fasteners 100 to vertebrae V.

In some embodiments, spinal rod 14 and a spinal rod 13, similar to spinal rod 14, are delivered along the surgical pathway to the surgical site adjacent vertebrae V. In some embodiments, spinal construct 12, which can include spinal rods 13, 14 and/or bone fasteners 100 can be delivered or implanted as pre-assembled components or can be assembled in situ. Spinal rods 13, 14 are positioned for disposal within implant cavity 108 of bone fasteners 100 to connect spinal rods 13, 14 with bone fasteners 100. In some embodiments, spinal rods 13, 14 may be attached with vertebrae V with a plurality of bone fasteners 100 over a plurality of vertebral levels. Spinal rods 13, 14 may be disposed with vertebrae in a side-by-side orientation along vertebrae V in a bi-lateral configuration with vertebrae V, as shown in FIG. 5, such that spinal rod 14 is disposed with a lateral side and spinal rod 13 is disposed with a contra-lateral side. In some embodiments, spinal rods 13, 14 are oriented in various configurations, as described herein. In some embodiments, a single spinal rod 14 is implanted with vertebrae V such that the implanted spinal rod is disposed in a uni-lateral configuration with vertebrae V.

In some embodiments, set screws 47 are torqued and threaded with threads of implant cavity 108 of selected bone fasteners 100 disposed cephalad and caudal to an apical curvature abnormality to secure spinal rod 14 with vertebrae V. Set screws 47 capture spinal rod 14 within implant cavity 108 of bone fasteners 100 without fixing spinal rod 14 relative to bone fasteners 100 disposed cephalad and caudal to the apical curvature such that longitudinal spinal growth of selected sections of vertebrae V is allowed. In some embodiments, set screws 47 are torqued and threaded with threads of implant cavity 108 of selected bone fasteners 100 disposed adjacent the apical curvature abnormality to fix spinal rod 14 with bone fasteners 100 such that bone fasteners 100 disposed adjacent the apical curvature abnormality resist relative movement of spinal rod 14.

Spinal construct 12 is surgically implanted beneath the scapula of the patient and muscle mass to prevent spinal construct 12 from protruding through skin of the patient. A practitioner manipulates spinal construct 12 to fix and/or attach spinal construct 12 with rib R1 of a rib cage RC and fix and/or attach spinal rod 14 with vertebrae V in a uni-lateral configuration. In some embodiments, a plurality of spinal constructs 12 are implanted in the patient and connected with spinal rod 14 and spinal rod 13 in a bilateral configuration with vertebrae V. Plate 16 is positioned such that hooks 24, 26 are disposed in contact with rib R1. A force is applied to plate 16 such that hooks 24, 26 space apart and translate over rib R1 and outer surface 2 of rib R1 engages with surfaces 28, 30 of hooks 24, 26, as described herein. Spinal rod 14 is provisionally locked within tissue cavity 32 and hooks 24, 26 prevent spinal rod 14 from disengaging from tissue cavity 32 during translation of plate 16 along spinal rod 14. Set screw 47 is axially translated through cavity 35 to prevent the disengagement of spinal rod 14 from cavity 35 while still allowing spinal rod 14 to translate about the coronal plane.

In some embodiments, spinal correction system 10 may include a spinal construct comprising one or a plurality of spinal constructs 12 that are each attachable with a selected vertebral level of vertebrae V, or two or more selected vertebral levels of vertebrae V. Spinal correction system 10 accommodates growth of vertebrae V of a selected section of the spine for correctional treatment to treat various spine pathologies, such as, for example, adolescent idiopathic scoliosis and Scheuermann's kyphosis.

In some embodiments, the components of spinal correction system 10 may be employed to treat progressive idiopathic scoliosis with or without sagittal deformity in either infantile or juvenile patients, including but not limited to prepubescent children, adolescents from 10-12 years old with continued growth potential, and/or older children whose growth spurt is late or who otherwise retain growth potential. In some embodiments, the components of spinal correction system 10 may be used to prevent or minimize curve progression in individuals of various ages.

In one embodiment, spinal correction system 10 includes an agent, which may be disposed, packed, coated or layered within, on or about the components and/or surfaces of spinal correction system 10. In some embodiments, the agent may include bone growth promoting material, such as, for example, bone graft to enhance fixation of the components and/or surfaces of spinal correction system 10 with vertebrae V. In some embodiments, the agent may include one or a plurality of therapeutic agents and/or pharmacological agents for release, including sustained release, to treat, for example, pain, inflammation and degeneration.

Upon completion of the procedure, the surgical instruments, assemblies and non-implanted components of spinal correction system 10 are removed and the incision is closed. Spinal correction system 10 can be made of radiolucent materials such as polymers. Radiomarkers may be included for identification under x-ray, fluoroscopy, CT or other imaging techniques. In some embodiments, the use of surgical navigation, microsurgical and image guided technologies may be employed to access, view and repair spinal deterioration or damage, with the aid of spinal correction system 10. In some embodiments, spinal correction system 10 may include one or a plurality of plates, connectors and/or bone fasteners for use with a single vertebral level or a plurality of vertebral levels.

Figure 6:
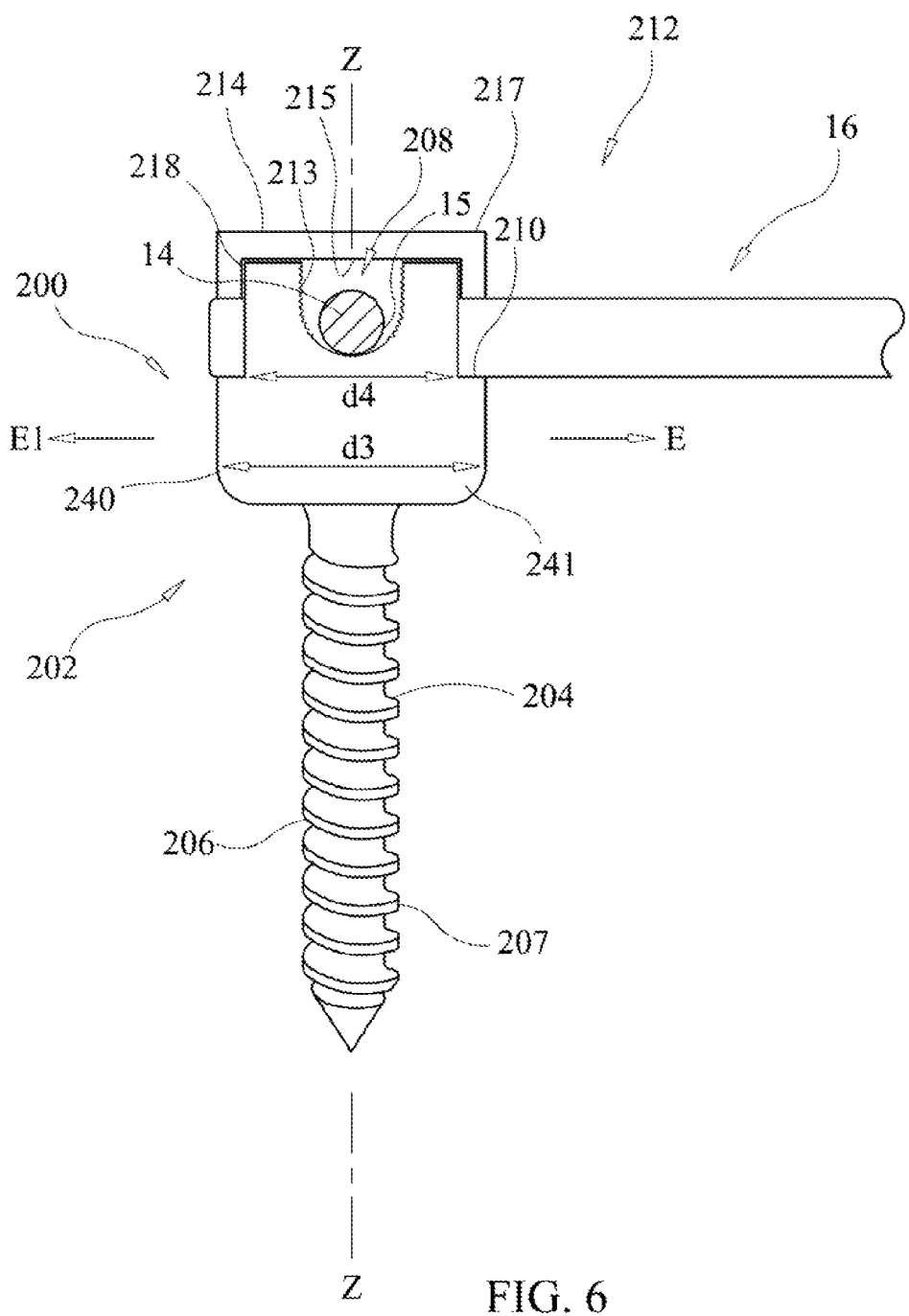
FIG. 6 is a side view in part cross-section of components of one embodiment of a system in accordance with the principles of the present disclosure.

In one embodiment, as shown in FIG. 6, system 10, similar to the systems and methods described with regard to FIGS. 1-5, comprises spinal construct 12, as described herein. A bone fastener 200, similar to bone fastener 100 described herein, includes a head 202 configured for disposal of spinal rod 14, and a shaft 204, similar to shaft 104, configured for penetrating tissue. Head 202 includes a base 241 defined by an outer surface 240. Head 202 includes a pair of spaced apart arms 218 defined by an outer surface 238 and an inner surface 213.

Inner surface 213 defines an implant cavity 208 that extends through head 202 and is configured for sliding disposal of spinal rod 14. Head 202 includes a shoulder 210, extending from base 241 and configured for disposal of plate 16. Shoulder 210 extends radially, in the direction shown by arrows E, E1, such that shoulder 210 extends circumferentially around arms 218. Head 202 has a diameter d3 defined by base 241 and a diameter d4 defined by arms 218. In some embodiments, shoulder 210 extends radially in the direction shown by arrows E, E1, such that diameter d3 is greater than diameter d4.

A detachable or removable cover 214 is engageable with plate 16 and bone fastener 200 to constrain spinal rod 14 within implant cavity 208. Cover 214 includes an inner surface 215 and an outer surface 217. Cover 214 is disposed on head 202 such that inner surface 215 is in contact with outer surface 238 of arms 218 such that spinal rod 14 is constrained within implant cavity 208. In one embodiment, cover 214 has a rectangular cross sectional configuration. In some embodiments, all or only a portion of cover 214 may have alternate cross sectional configurations, such as, for example, oval, oblong, triangular, square, polygonal, irregular, uniform, non-uniform, offset, staggered, undulating, arcuate, variable and/or tapered. In some embodiments, all or only a portion of surfaces 215, 217 may have alternate surface configurations to enhance fixation with tissue such as, for example, rough, arcuate, undulating, mesh, porous, semi-porous, dimpled and/or textured.

Shaft 204 of bone fastener 200 is configured with a cylindrical cross section and includes an outer surface 206 having an external thread form 207, similar to that described herein.

Figure 7:
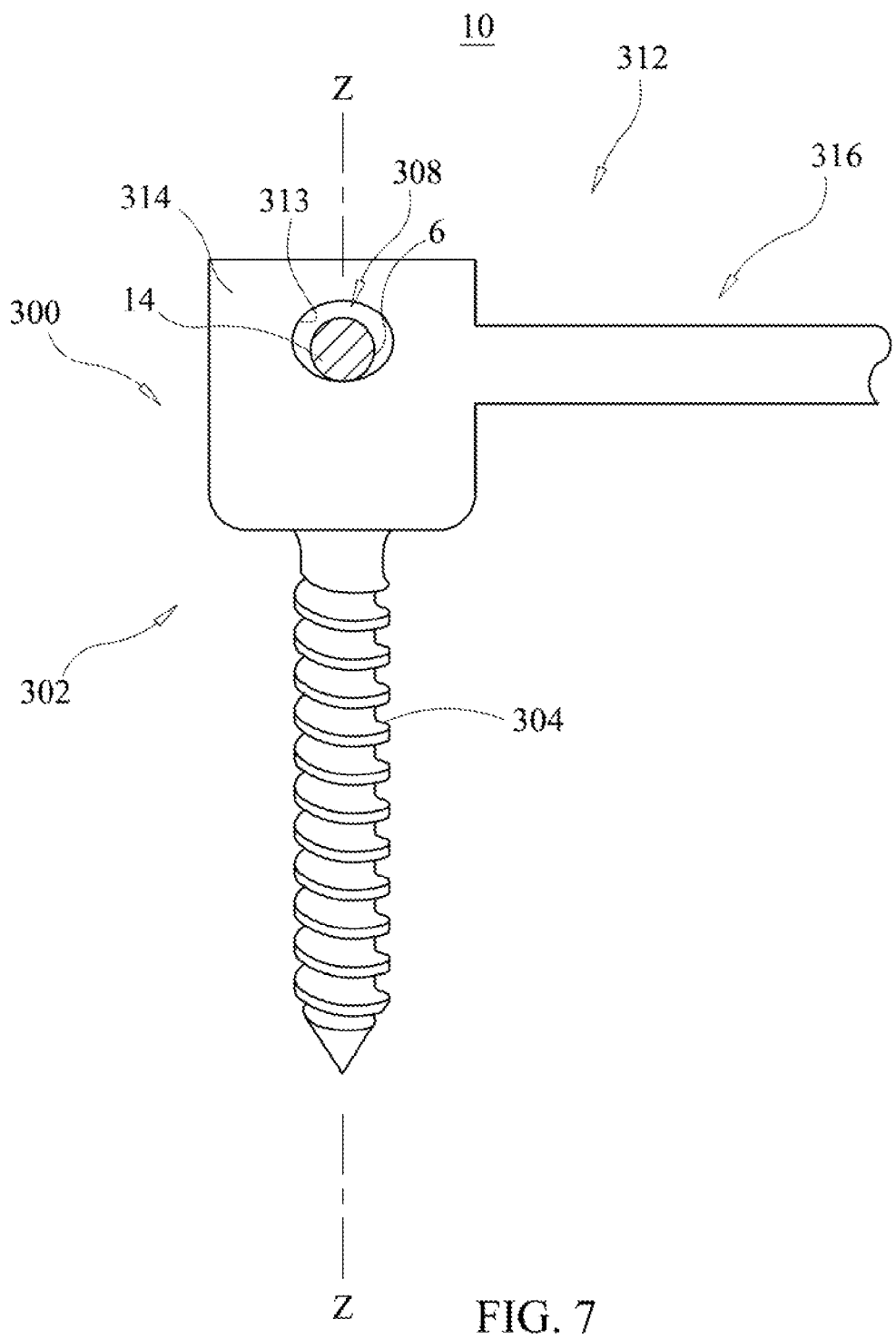
FIG. 7 is a side view in part cross-section of components of one embodiment of a system in accordance with the principles of the present disclosure.

In one embodiment, as shown in FIG. 7, system 10, similar to the systems and methods described herein, comprises spinal construct 12, as described herein. A bane fastener 300, similar to the bone fasteners described herein, includes a head 302 configured for disposal of spinal rod 14, and shaft 304 configured for penetrating tissue. Head 302 is integrally formed with a member, such as plate 316, similar to plate 16 described herein. Head 302 includes an outer surface 340 and an implant cavity 308 having an inner surface 313. Implant cavity 308 extends through head 302 and is configured for sliding disposal of spinal rod 14, as described herein. Head 302 is integrally formed with plate 316 to constrain spinal rod 14 while still allowing for vertebral growth, as described herein. In some embodiments, head 302 is monolithically formed with plate 316.

Figure 8:
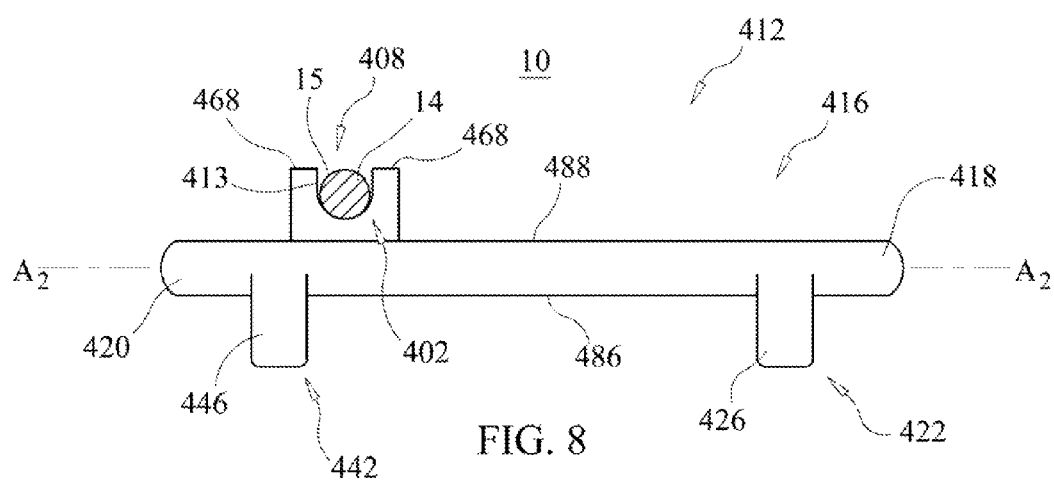
FIG. 8 is a side view in part cross-section of components of one embodiment of a system in accordance with the principles of the present disclosure.
Figure 9:
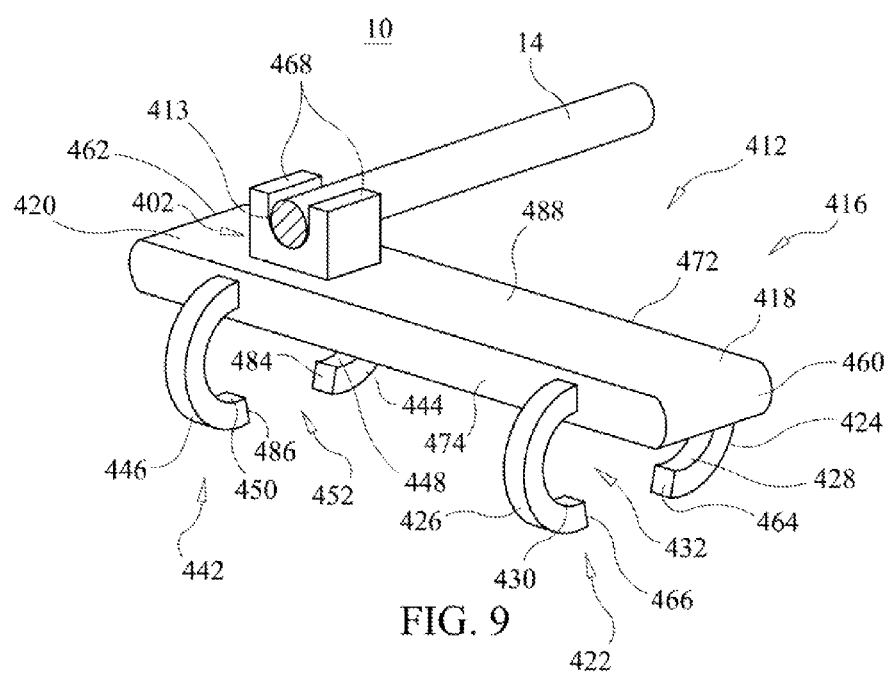
FIG. 9 is a perspective view of the components shown in FIG. 8.

In one embodiment, as shown in FIGS. 8 and 9, spinal system 10, similar to the systems and methods described herein, includes a spinal construct 412, similar to spinal construct 12 described herein. Spinal construct 412 is configured for connecting to tissue of a rib cage RC and tissue of vertebrae V, to correct spinal disorders, such as, for example, those described herein.

Spinal construct 412 includes a member, such as, for example, plate 416, similar to plate 16 described with regard to FIGS. 1-5, extending between an end 418 and an end 420. Plate 416 has a rectangular configuration and a thickness T1 defined by walls 472, 474.

Plate 416 includes parts, such as, for example clip 422 and a clip 442, similar to clip 22 described herein, configured for connecting to tissue, such as, for example, rib R1 of a rib cage and tissue of vertebrae V. Clips 422, 442 are configured to extend laterally from walls 472, 474 and from ends 418, 420. Each clip 422 and 442 has a claw configuration including a pair of resilient, inwardly biased arms, such as, for example, a hook 424 and a hook 426 of clip 422, and a hook 444 and a hook 446 of second clip 442.

Hooks 424, 426, 444, 446 are configured for direct connection to plate 416 and pivotally movable therefrom. Hooks 424, 426 are connected to a pivot point 460 adjacent opening 432. Hooks 444, 446 are connected to a pivot point 462 adjacent opening 452.

Hooks 424, 426 include bevel surfaces 464, 466, respectively, at an end of hooks 424, 426 opposite pivot point 460 to facilitate insertion of tissue into tissue cavity 432, similar to tissue cavity 32, as described herein. Hooks 444, 446 include bevel surfaces 484, 486, respectively, at an end of hooks 444, 446 opposite pivot point 462 to facilitate insertion of tissue into tissue cavity 452, as described herein. In some embodiments, all or only a portion of beveled surfaces 464, 466, 484, 486 may have various surface configurations, such as, for example, rough, arcuate, undulating, porous, semi-porous, dimpled, polished and/or textured, to enhance engagement of tissue. In some embodiments, beveled surfaces 464, 466, 484, 486 may be variously configured and dimensioned, such as, for example, planar, concave, convex, polygonal, irregular, uniform, non-uniform, staggered, tapered, consistent or variable.

Hook 424 includes a surface 428. Hook 426 includes a surface 430. Surfaces 428, 430 have an arcuate configuration defining tissue cavity 432 configured to capture tissue of the rib cage therebetween. In some embodiments tissue cavity 432 is expandable to receive tissue, such as rib R1 such that surfaces 428, 430 space apart to receive tissue and are biased to contract such that surfaces 428, 430 engage tissue for capture of tissue with hooks 424, 426, as described herein. In some embodiments, surfaces 428, 430 are configured to facilitate the relative movement of hooks 424, 426 and expansion of tissue cavity 432 such that surfaces 428, 430 are movable to dispose tissue with hooks 424, 426. In some embodiments, hooks 424, 426 are variously configured, such as, for example, round, oval, oblong, irregular, uniform, non-uniform, consistent, variable, horseshoe shape, U-shape or kidney bean shape.

In some embodiments, surface 428 is oriented in a first direction and surface 430 is oriented in a second, opposite direction such that surfaces 428, 430 face each other and are configured to engage opposite sides of an outer surface of a rib R1 of a rib cage RC. In some embodiments, surfaces 428, 430 define an adjustable tissue cavity 432 configured for selective capture of rib cage RC. In some embodiments, tissue cavity 432 has a cross sectional area selectively adjustable to be substantially equal to a cross sectional area of rib R1 of rib cage RC. In one embodiment, tissue cavity 432 is variously configured, such as, for example, oval, oblong, triangular, rectangular, square, polygonal, irregular, uniform, non-uniform, horseshoe shape, U-shape, kidney bean shape, variable and/or tapered.

Hook 444 includes a surface 448. Hook 446 includes a surface 450. In some embodiments, all or only a portion of surfaces 448, 450 may have alternate surface configurations, such as, for example, planar, rough, undulating, porous, semi-porous, dimpled, polished and/or textured. In some embodiments, surfaces 448, 450 may have an arcuate configuration defining tissue cavity 452 configured to capture tissue of the rib cage therebetween. In some embodiments, tissue cavity 452 is expandable to receive vertebral tissue such as, for example, vertebrae V such that surfaces 448, 450 space apart to receive tissue and are biased to contract such that surfaces 448, 450 engage tissue for capture of tissue within hooks 444, 446, as described herein. In some embodiments, surfaces 448, 450 are configured to facilitate the relative movement of hooks 444, 446 and expansion of tissue cavity 452 such that surfaces 448, 450 are movable to dispose tissue with hooks 444, 446. In some embodiments, hooks 444, 446 are variously configured, such as, for example, round, oval, oblong, irregular, uniform, non-uniform, consistent, variable, horseshoe shape, U-shape or kidney bean shape.

Surface 448 is oriented in a first direction and surface 450 is oriented in a second, opposite direction such that surfaces 448, 450 face each other and are configured to engage opposite sides of an outer surface of tissue. In some embodiments, surfaces 448, 450 define an adjustable tissue cavity 452 configured for selective capture of tissue of rib cage RC and/or vertebrae V. Tissue cavity 452 has a cross sectional area selectively adjustable to be substantially equal to a cross sectional area of rib cage RC and/or vertebrae V. In one embodiment, tissue cavity 452 is variously configured, such as, for example, oval, oblong, triangular, rectangular, square, polygonal, irregular, uniform, non-uniform, horseshoe shape. U-shape, kidney bean shape, variable and/or tapered.

Plate 416 includes a surface 488 oriented in a first direction and a surface 486 oriented in a second direction, opposite the first direction, as shown in FIG. 8. End 420 includes a receiving member 402 on surface 488 comprising a pair of spaced apart arms 468 defining an implant cavity 408. Spinal rod 14 is slidably disposable in implant cavity 408 such that outer surface 15 of spinal rod 14 engages inner surface 413 of implant cavity 408 such that plate 416 can be translated along spinal rod 14 to a desired position.

In some embodiments, implant cavity 408 has a cross sectional configuration corresponding to the cross sectional configuration of spinal rod 14 to resist and/or prevent rotation of spinal rod 14 therein. In some embodiments, implant cavity 408 has a cross sectional area substantially equal to a cross sectional area of spinal rod 14 such that spinal rod 14 is axially translatable through implant cavity 408 relative to plate 416. In some embodiments, inner surface 413 includes a layer of friction-reducing material (not shown). In some embodiments, the layer may include an insert and/or coating comprising silicone, poly(tetrafluororthene), lubricants and/or material examples as described herein. The layer of friction-reducing material provides an even interface between inner surface 413 of implant cavity 408 and outer surface 15 of spinal rod 14. In some embodiments, all or only a portion of inner surface 413 may have alternate surface configurations, such as, for example, planar, rough, undulating, porous, semi-porous, dimpled, polished and/or textured. In some embodiments all or only a portion of implant cavity 408 may have alternate surface configurations, such as, for example, planar, rough, undulating, porous, semi-porous, dimpled, polished and/or textured. In some embodiments, implant cavity 408 is variously shaped, such as, for example, oval, oblong, rectangular, triangular, circular, square, polygonal, uniform, non-uniform, variable, tubular and/or tapered.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:
1. A spinal construct comprising:
    at least one spinal implant configured to be connected with vertebrae; and
    a member extending between a first end and a second end configured for connection with the at least one spinal implant, the member extends along a first plane and includes a clip extending laterally from the first end in a second plane oriented transverse to the first plane, the clip includes inwardly biased arms for capturing tissue of a rib cage, wherein the clip is configured for movement between an expandable orientation to receive tissue and a contracted orientation to capture tissue, wherein a plate defines an opening configured for disposal of a bone fastener of the at least one implant, wherein the at least one implant includes a spinal rod connected with the bone fastener, and wherein the spinal construct further comprises a cover engageable with the plate and the bone fastener to attach the spinal rod with the bone fastener.

2. A spinal construct as recited in claim 1, wherein the clip has a claw configuration for capturing tissue.

3. A spinal construct as recited in claim 1, wherein the clip defines a cavity configured to capture a portion of tissue.

4. A spinal construct as recited in claim 1, wherein the clip is configured for dynamic movement between the expandable orientation and the contracted orientation.

5. A spinal construct as recited in claim 1, wherein the clip is biased in the contracted orientation.

6. A spinal construct as recited in claim 1, wherein the clip comprises a first hook including a surface oriented in a first direction and a second hook including a surface oriented in a second direction.

7. A spinal construct as recited in claim 1, wherein the second end is configured for movement relative to the spinal implant.

8. A spinal construct as recited in claim 1, wherein the second end is rotatable relative to the at least one implant in a coronal plane of the vertebrae.

9. A spinal construct as recited in claim 1, wherein the spinal implant includes a bone fastener comprising a head, the member being connected to the head.

10. A spinal construct as recited in claim 9, wherein the bone fastener includes a shoulder disposed about a portion of the head and configured for disposal of the member.

11. A spinal construct as recited in claim 1, wherein the member includes a plate.

12. A spinal construct as recited in claim 1, wherein the cover is movable relative to the plate.

13. A spinal construct as recited in claim 1, wherein an end of the member includes spaced arms for disposal of the spinal implant and a claw configuration for capturing tissue.

14. A spinal construct comprising:
at least one implant configured to be connected with vertebrae; and
a plate extending in a first plane between a first end including a clip extending laterally relative to the plate in a second plane oriented transverse to the first plane, the clip having inwardly biased arms for capturing tissue of a rib cage and a second end defining a cavity configured for disposal of the at least one implant,
wherein the plate defines an opening configured for disposal of a bone fastener of the at least one implant,
wherein the at least one implant includes a spinal rod connected with the bone fastener, and
wherein the spinal construct further comprises a cover engageable with the plate and the bone fastener to attach the spinal rod with the bone fastener.

15. A spinal construct as recited in claim 14, wherein the second end is rotatable relative to the at least one implant in a coronal plane of the vertebrae.

16. A spinal construct as recited in claim 14, wherein the cover is movable relative to the plate.

17. A spinal construct comprising:
a bone fastener configured to be connected with vertebrae;
a spinal rod connected with the bone fastener; and
a member extending in a first plane between a first end including a clip configured for connection to tissue of a rib cage and a second end configured for connection with the spinal rod, the clip extends laterally relative to the member in a second plane oriented transverse to the first plane, the clip is configured for movement between an expandable orientation to receive tissue and a contracted orientation to capture a portion of the rib cage,
wherein the member is a plate comprising an opening configured for disposal of the bone fastener,
wherein the spinal rod is connected with the bone fastener, and
wherein the spinal construct further comprises a cover engageable with the plate and the bone fastener to attach the spinal rod with the bone fastener.

* * * * *